United States Patent
Rigault et al.

(10) Patent No.: US 6,389,428 B1
(45) Date of Patent: May 14, 2002

(54) SYSTEM AND METHOD FOR A PRECOMPILED DATABASE FOR BIOMOLECULAR SEQUENCE INFORMATION

(75) Inventors: Philippe E. Rigault, Palo Alto; Anne L. Curtis, Pacifica; Richard D. Goold, Belmont; David A. Hadley, Palo Alto; Harold H. Hibbert, Fremont; Tod M. Klingler, San Carlos; Robert E. Lagace, San Francisco; Laura L. Stuve, Los Gatos; Michael G. Walker, Sunnyvale; Michael P. Wood, San Francisco, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/797,653

(22) Filed: Apr. 11, 2001

Related U.S. Application Data

(63) Continuation of application No. 09/175,738, filed on Oct. 20, 1998, now Pat. No. 6,223,186.
(60) Provisional application No. 60/084,027, filed on May 4, 1998.

(51) Int. Cl.[7] .............................................. G06F 17/30
(52) U.S. Cl. ..................... 707/104.1; 707/6; 707/100; 702/19; 435/6
(58) Field of Search .............. 707/2, 5–10, 100–109.1, 707/102, 104.1, 200; 702/19–20; 435/6; 714/763; 710/74; 709/200, 201, 202; 711/203; 717/5

(56) References Cited

U.S. PATENT DOCUMENTS

| | | | |
|---|---|---|---|
| 5,295,256 A | | 3/1994 | Bapat .......................... 707/100 |
| 5,392,428 A | | 2/1995 | Robins .......................... 707/1 |
| 5,524,253 A | * | 6/1996 | Pham et al. ................. 709/202 |
| 5,537,592 A | * | 7/1996 | King et al. .................. 707/200 |
| 5,577,249 A | | 11/1996 | Califano ..................... 707/100 |
| 5,604,843 A | * | 2/1997 | Shaw et al. ................... 358/1.1 |
| 5,706,498 A | | 1/1998 | Fujimiya et al. ............... 707/6 |
| 5,729,710 A | * | 3/1998 | Magee et al. ............... 711/203 |
| 5,953,727 A | | 9/1999 | Maslyn et al. .............. 707/104 |
| 5,960,200 A | * | 9/1999 | Eager et al. .................... 717/5 |
| 5,970,500 A | | 10/1999 | Sabatini et al. ............. 707/104 |
| 6,023,659 A | | 2/2000 | Seilhamer et al. ............ 702/19 |
| 6,065,037 A | * | 5/2000 | Hitz et al. ................... 709/200 |
| 6,321,358 B1 | * | 11/2001 | Anderson ................... 714/763 |

OTHER PUBLICATIONS

Bergholz, Andre et al., "Sequence Comparision Using a Relational Database Approach," Proceedings of the 1997 International Database Engineering and Applications Symposium, IDEAS '97, Aug. 25–27, 1997, pp 126–131.

Cheang, In Kuan et al., "Overview of the Structures of Heterogeneous Genome Databases," Proceedings of the Twenty–Seventh Hawaï International Conference on Biotechnology Computing, System Science, 1994, vol. V, Jan. 4–7, 1994, pp. 15–24.

(List continued on next page.)

*Primary Examiner*—Hosain T. Alam
*Assistant Examiner*—Shahid Alam
(74) *Attorney, Agent, or Firm*—Squire, Sanders & Dempsey LLP

(57) ABSTRACT

A computer system stores biomolecular data in a database in a memory. The biomolecular database has a set of entities. Each entity stores attributes for a plurality of entries. At least one attribute is stored in an array. Data associated with an entry is stored at a location in the array. An entity offset designates the location of the data in the array. The same entity offset value is used to access data associated with a particular entry for all attributes within the entity.

31 Claims, 10 Drawing Sheets

OTHER PUBLICATIONS

Sastry, Raghu et al., "A Systolic Array for Approximate String Matching," Proceedings of the 1993 IEEE International Conference on Computer Design: VLSI in Computers and Processors, ICCD '93, Oct. 3–6, 1993, pp. 402–405.

S. Karlin, et al., "Applications and Statistics for Multiple High–Scoring Segments in Molecular Sequences," (Jun. 1993) Proc. Natl. Acad. Sci. USA, vol. 90, pp. 5873–5877.

S. Karlin, et al., "Methods for Assessing the Statistical Significance of Molecular Sequence Features by Using General Scoring Schemes," (Mar. 1990) Proc. Natl. Sci. USA, vol. 87 pp. 2264–2268.

* cited by examiner

SYSTEM AND METHOD FOR A PRECOMPILED DATABASE FOR BIOMOLECULAR SEQUENCE INFORMATION

The present application is a continuation of U.S. patent application Ser. No. 09/175,738, entitled "SYSTEM AND METHOD FOR A PRECOMPILED DATABASE FOR BIOMOLECULAR SEQUENCE INFORMATION," filed Oct. 20, 1998, now U.S. Pat. No. 6,223,186 which claims the benefit of U.S. Provisional Patent Application No. 60/084,027, entitled "MODULAR DATABASE AND SYSTEM," filed May 4, 1998. U.S. patent application Ser. No. 09/175,738 and U.S. Provisional Patent Application No. 60/084,027 are both incorporated by reference herein for all purposes.

The present invention relates generally to a system and method for storing and retrieving biomolecular sequence information. More particularly, the invention relates to a system and method for storing biomolecular sequence information in a precompiled, modular format which allows for rapid retrieval of the information.

BACKGROUND OF THE INVENTION

Informatics is the study and application of computer and statistical techniques to the management of information. In genome projects, bioinformatics includes the development of methods to search databases quickly, to analyze nucleic acid sequence information, and to predict protein sequence and structure from DNA sequence data. Increasingly, molecular biology is shifting from the laboratory bench to the computer desktop. Advanced quantitative analyses, database comparisons, and computational algorithms are needed to explore the relationships between sequence and phenotype.

One use of bioinformatics involves studying genes differentially or commonly expressed in different tissues or cell lines such as in normal or cancerous tissue. Such expression information is of significant interest in pharmaceutical research. A sequence tag method is used to identify and study such gene expression. Complementary DNA (cDNA) libraries from different tissue or cell samples are available. cDNA clones, or expressed sequence tags (ESTs) that cover different parts of the mRNA(s) of a gene are derived from the cDNA libraries. The sequence tag method generates large numbers, such as thousands, of clones from the cDNA libraries. Each cDNA clone can include about 100 to 800 nucleotides, depending on the cloning and sequencing method. Assuming that the number of sequences generated is directly proportional to the number of mRNA transcripts in the tissue or cell type used to make the cDNA library, then variations in the relative frequency of occurrence of those sequences can be stored in computer databases and used to detect the differential expression of the corresponding genes.

Sequences are compared with other sequences using heuristic search algorithms such as the Basic Alignment Search Tool (BLAST). BLAST compares a sequence of nucleotides with all sequences in a given database. BLAST looks for similarity matches, or 'hits', that indicate the potential identity and function of the gene. BLAST is employed by programs that assign a statistical significance to the matches using the methods of Karlin and Altschul (Karlin S., and Altschul, S. F. (1990) Proc. Natl. Acad. Sci. U S A. 87(6): 2264–2268; Karlin, S. and Altschul, S. F. (1993) Proc. Natl. Acad. Sci. U S A. 90(12): 5873–5877). Homologies between sequences are electronically recorded and annotated with information available from public sequence databases such as GenBank. Homology information derived from these and other comparisons provides a basis for assigning function to a sequence.

Typically computer systems use relational databases to store, process, and manipulate nucleotide and amino acid sequences, expression information, chromosomal location, and protein function information. As the amount of biomolecular information increases, the computer systems and their databases must accommodate the storage, retrieval, comparison, and display of very large amounts of data. Typically, the data is stored in multiple files making up a relational database. Each file has records with predefined fields. Records are accessed using at least one field that is designated as a key or index. Relational databases typically use a join operation to cross reference data stored in different files based on a common key field. The join operation basically combines data stored in multiple files. However, if one of the files being joined, such as the cDNA or clone file, is unusually large, then even a simple join operation with a small file is time consuming and slow.

In addition relational databases use separate data and index files. Index files are used to access information in corresponding data files. Typically, a large amount of storage is needed to store both the data and index files. Therefore, in a system with many data and index files, it is unlikely that all data can be stored at any one time in the main memory of the computer system. The data that remains on the disk must be swapped into main memory. The swapping of data into main memory further contributes to the slow response time of data retrieval systems having unusually large database tables.

Therefore, there is a need for a biomolecular database that eliminates the need for using join operations. In addition, there is a need for a biomolecular database that can be stored in the main memory of ordinary desktop computer systems. There is also a need for a biomolecular database with a common set of tissue classes that can assign a cDNA library to many different tissue classes.

The present invention provides a self-sufficient modular database that organizes and precompiles data to eliminate the need for using join operations. In addition, the database is organized such that the entire database can be stored in the main memory of the computer system. The present invention also provides a way to associate a cDNA library with multiple tissue classes.

SUMMARY OF THE INVENTION

A computer system stores biomolecular data in a database in a memory. The biomolecular database has a set of entities. Each entity stores attributes for a plurality of entries. At least one attribute is stored in an array. Data associated with an entry is stored at a location in the array. An entity offset designates the location of the data in the array. The same entity offset value is used to access data associated with a particular entry for all attributes within the entity.

The modular database allows extremely rapid search, comparison, and retrieval of information from very large databases. In the database, joins are eliminated through the use of a set of predefined addressing techniques. The data is organized into entities and the relationships of the data between entities is pre-compiled. Offsets or pointers define relationships between entities. Although entity offsets may be stored in multiple locations, the biomolecular data is stored once.

The addressing technique allows for rapid searching and comparisons of very large amounts of sequence data. Such rapid processing of sequence information provides the capability for significant analysis of the biological function of the huge numbers of sequences currently residing in public and private databases.

The present invention also provides a database and system that allows for comparison of libraries. Library comparison techniques include direct comparisons of sequence expression between libraries that were derived from normal and diseased tissues to provide expression information useful for identifying target molecules for pharmaceutical therapy.

In addition, the present invention provides a database that is structured so as to facilitate quick access to expression level information for a specified cluster or set of clusters of sequences in a specified set of libraries (each of which represents a specific source of expression information). The present invention also provides tools for quickly determining the sensitivity and specificity of expression level values.

The invention also provides an improved technique for assessing similarities between sequences and clustering multiple sequences.

The modular database increases the speed of analyzing sequences which will help accelerate biomolecular research for numerous applications.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENTS

Figure 1:
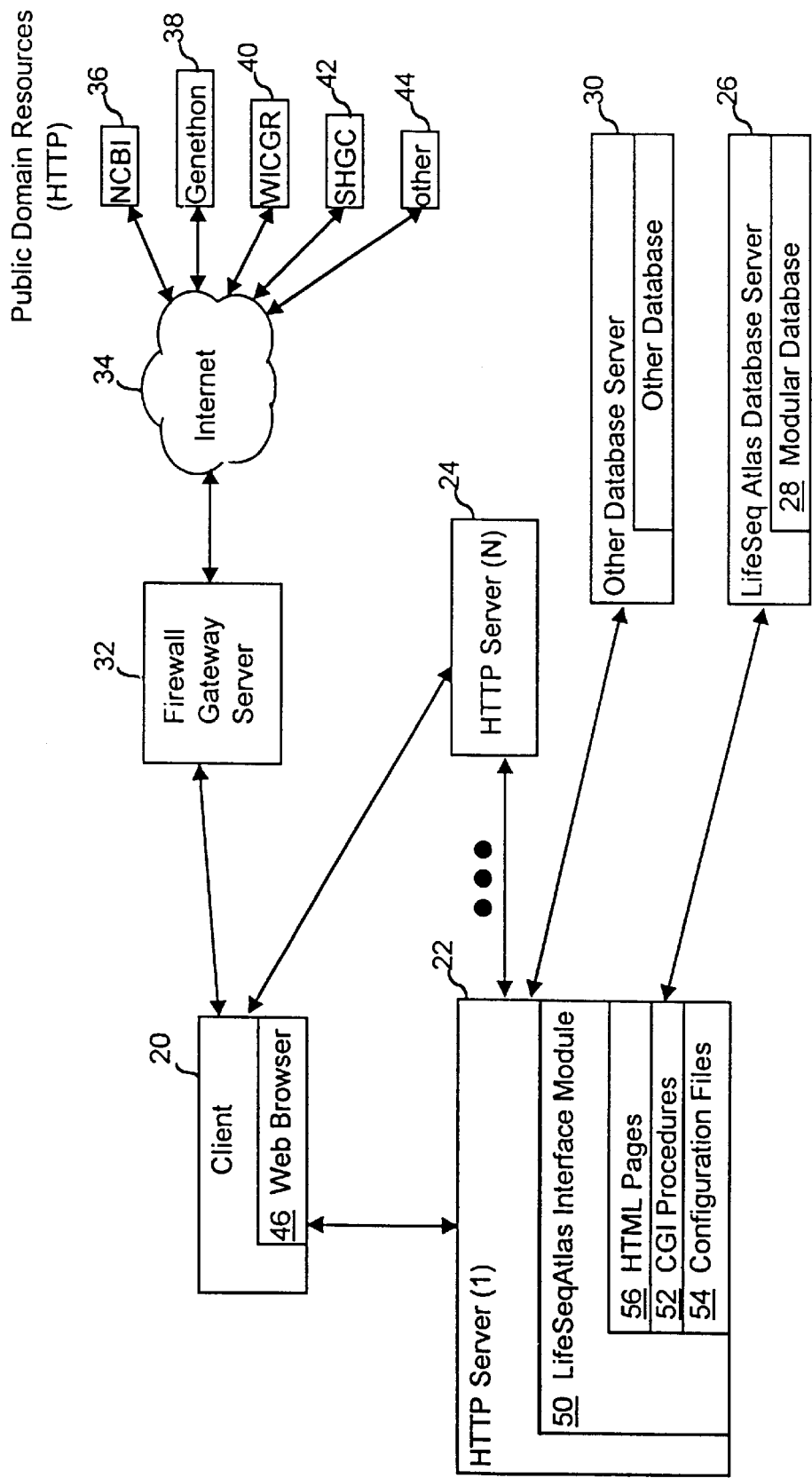
FIG. 1 is a diagram of a client-server system suitable for use with the present invention.

FIG. 1 depicts a network system for retrieving information stored in the biomolecular database of the present invention. The major computer system components of the network are:

at least one client computer system 20, multiple HTTP servers 22, 24 to access the world-wide-web (WWW), a LifeSeq Atlas Database Server 26 that stores the modular database 28, another data base server 30, and a firewall gateway server 32 that connects to the Internet 34.

The client computer system 20 connects to at least one HTTP server, 22, 24, that is used to access the world wide web. The network can have multiple servers, server (1) 22 to server (N) 24. In an alternate embodiment, to ensure high availability, the system automatically switches between the servers if one of the servers becomes unavailable. The client system 20, via the firewall gateway server 32, also has access to public domain resources 36, 38, 40, 42 and 44 on the Internet 34. On the client computer system 20, a user runs web browser software 46 to access both the public domain resources 36, 38, 40, 42 and 44 and the biomolecular data in the modular database 28.

One of the HTTP servers, HTTP Server 1, 22 stores and executes the LifeSeq Atlas interface module 50 to process user requests for data. The LifeSeq Atlas Interface module 50 includes many types of modules such as CGI procedures 52, configuration files 54 and HTML pages 56. The CGI procedures 52 allow the client web browser 46 to access data stored on the LifeSeq Atlas database server 26. The configuration files 54 store the paths where the local resources reside, such as BLAST files and also store the URLs of outside resources. The HTML pages 56 are static documents that are transmitted to the client Web browser 46 and may include HTTP hyperlinks to other resources.

The client system 20, HTTP servers 22, 24, the LifeSeq Atlas database server 26 and the other database server 30 may be networked via an intranet using TCP/IP protocol. The servers 22, 24, 26, 30 and 32 may be UNIX workstations having 512 MB of main memory, a F4VSCSI-2 adapter or Fiber Link Disk Controller, a CD-ROM Drive, an internal floppy disk drive X560A and multiprocessor systems with at least four processors. The client computer system 20 can be a personal computer or UNIX workstation.

Figure 2:
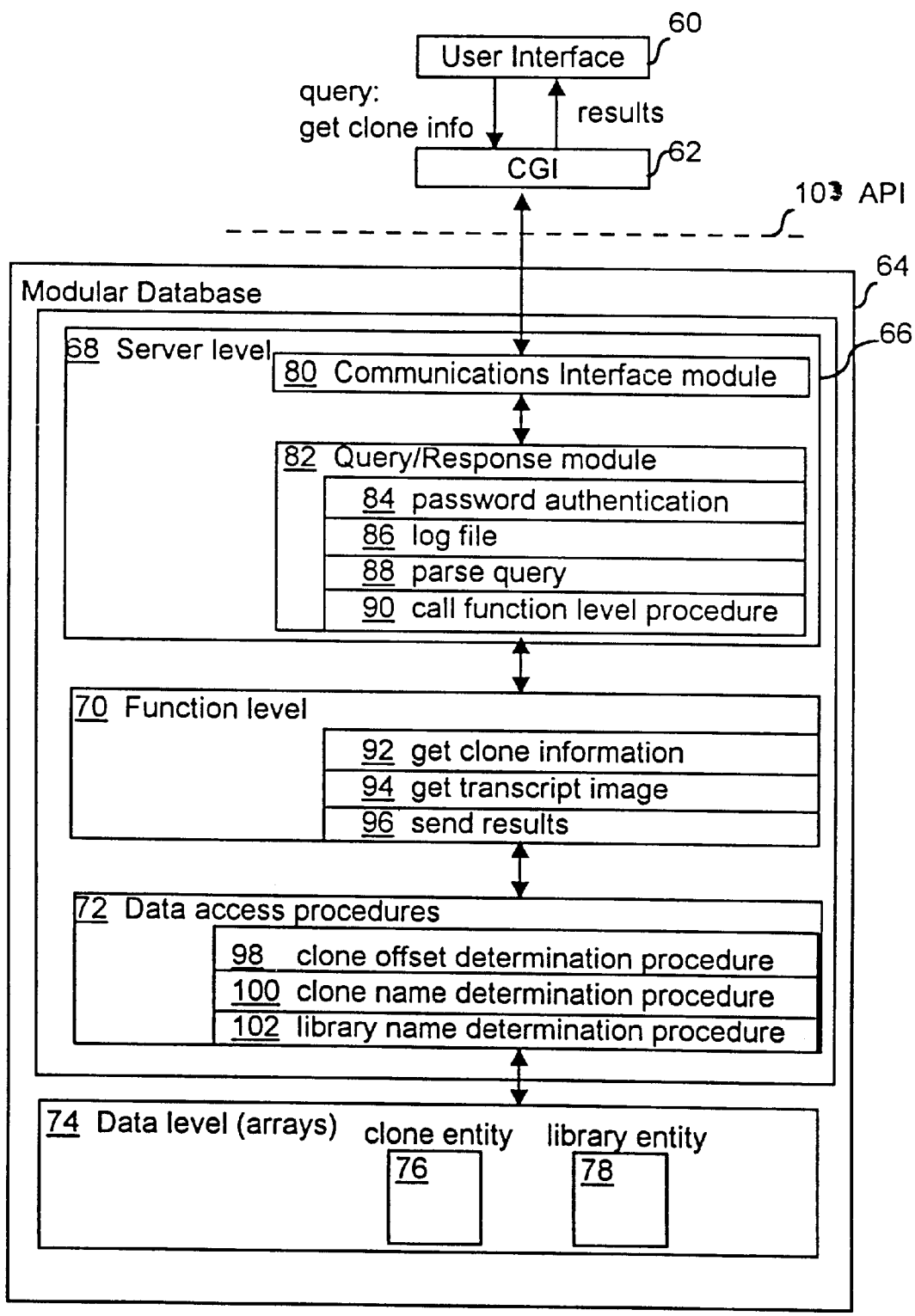
FIG. 2 is depicts the modules of the modular database system in connection with user interface.

FIG. 2 shows the flow of information between the various modules of the system to generate a response to a user's query of the modular database. The client computer's web browser provides a graphical user interface (GUI) 60 that allows the user to graphically construct search requests to retrieve data from the databases. The GUI 60 includes well-known elements such as buttons, pull down menus, and scroll bars that provide a way for the user to construct the search request.

The user selects parameters and the desired information using the GUI 60 of the web browser (46, FIG. 1). The web browser 46 passes the input to a CGI script 62 on one of the HTTP servers. The CGI script 62 sends a string of commands and passes the input to the modular database module 64 which returns the requested data to the CGI script 62. The CGI script uses HTTP protocol. The CGI script 62 sends the data back to the HTTP server. The HTTP server passes the data back to the user's web browser 46 and the results are displayed on the GUI 60 on the client computer.

The software modules of the modular database 66 form a hierarchy having a server level 68, a function level 70, and data access procedures 72. A data level 74 includes the entities (e.g., database tables) that store the biomolecular data such as the clone entity 76 and the library entity 78.

In the server level 68, a communications interface module 80 communicates with the CGI procedures 62 using UNIX sockets. The communication interface 80 receives commands from the CGI procedures 62 and sends the commands to the query/response module 82. The query/response module 82 has modules that authenticate a password 84 that is part of the command, generate or update a log file 86, and parse the command 88. The query/response module 82 also has a module 90 that calls a function level procedure in response the parsed command.

The function level 70 has modules or procedures that accumulate the data for the different types of queries available from the user interface. In other words, the function level modules 70 populate predefined structures with data and return the predefined structures to the query/response module 82, and will call various data access procedures 72 to retrieve the requested information from the data level 74. For example, the function level 70 includes procedures such as get clone information 92, get transcript image 94 and a function to send results to the query/response module 96.

The data access procedures 72 are the lowest level procedures and retrieve the biomolecular data from the entities 76, 78 of the modular database 74. Exemplary procedures comprise a clone offset determination procedure 98, a clone name determination procedure 100 and a library name determination procedure 102. After the requested data is retrieved, the function level 70 returns the data to the query/response module 82. In response to the query/response module 82, the communications interface 80 opens a socket and transmits the data to the CGI procedure 62.

One advantage of the modular database is that the database provides a consistent Application Programming Interface (API) 103. Even if the database schema changes, the user interface 60 and CGI procedures 62 need not be changed.

Structure of the Database

The database stores precompiled biomolecular data and organizes the biomolecular information into entities (e.g., database tables). Each entity has a set of attributes (sometimes called the columns of a database table). Generally, information for an attribute is stored in an array or database table. Each array has multiple entries. For a particular entry of an entity, the same offset value provides access to all the attribute information for that entry within that entity. For instance, if the offset for a particular entry is 11225, then all the attribute information for that entry will be found at offset 11225 in the various attribute arrays for the entity. Each array may be stored in a separate file.

The following naming convention will be used to refer to an attribute of an entity: "entity name. attribute name."

Figure 3A:
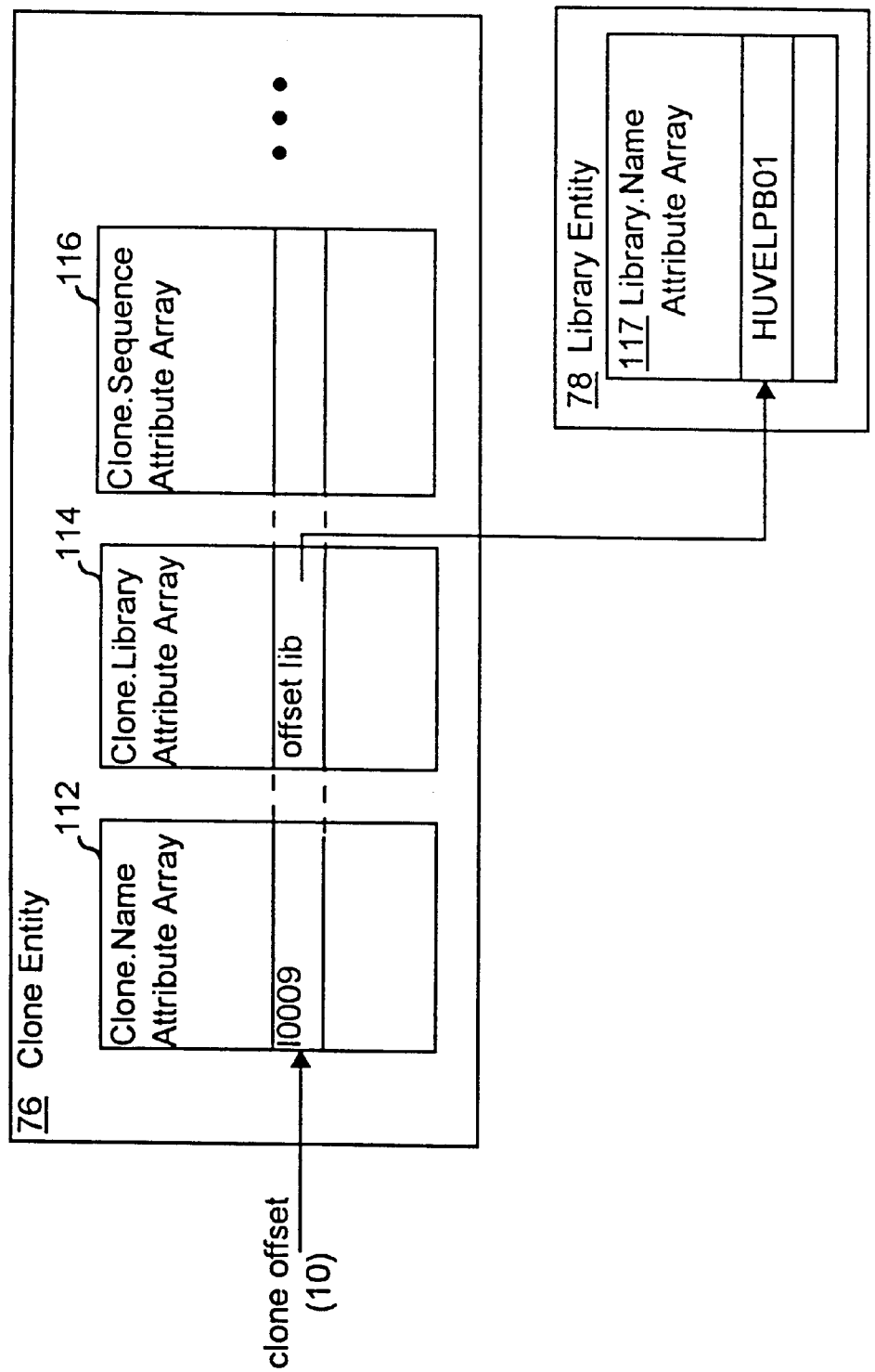
FIG. 3A is an exemplary clone entity with several exemplary attribute arrays.

FIG. 3A shows an exemplary portion of a clone entity 76 with clone.name 112, clone.library 114 and clone.sequence 116 attribute arrays. As shown by the dashed lines of FIG. 3A, a single clone offset (e.g., with a value of "10") points to the location or address in which information for a particular clone is stored in all the clone entity arrays. in other words, the attribute information for the $10^{th}$ clone in the clone entity is located at clone.name(10), clone.library(10) and clone.sequence(10).

In the present discussion, the term "location" refers to the "logical" location of the information, as opposed to its physical location in memory. Arrays are made up of a repeating data structure. Because arrays can use different data structures, the same logical location for different arrays may generate very different physical addresses.

An entity stores three types of data: absolute or actual data, offset data, and POS structures. FIG. 3A shows an example of absolute data in which the clone offset 10 points to an entry having a clone name of I0009 in the clone.name attribute array.

The offset data is used to define the relationships among the entries of the entities. In FIG. 3A, as an example of offset data, the clone.library attribute array 114 does not store a library name, but stores an appropriate offset value, shown as "offset lib," which is used to access the corresponding entry storing "HUVELPB01" in the library.name attribute array 117 of the library entity 78. The use of offset data reduces the amount of absolute data stored in the database thereby reducing the size of the database.

Figure 3B:
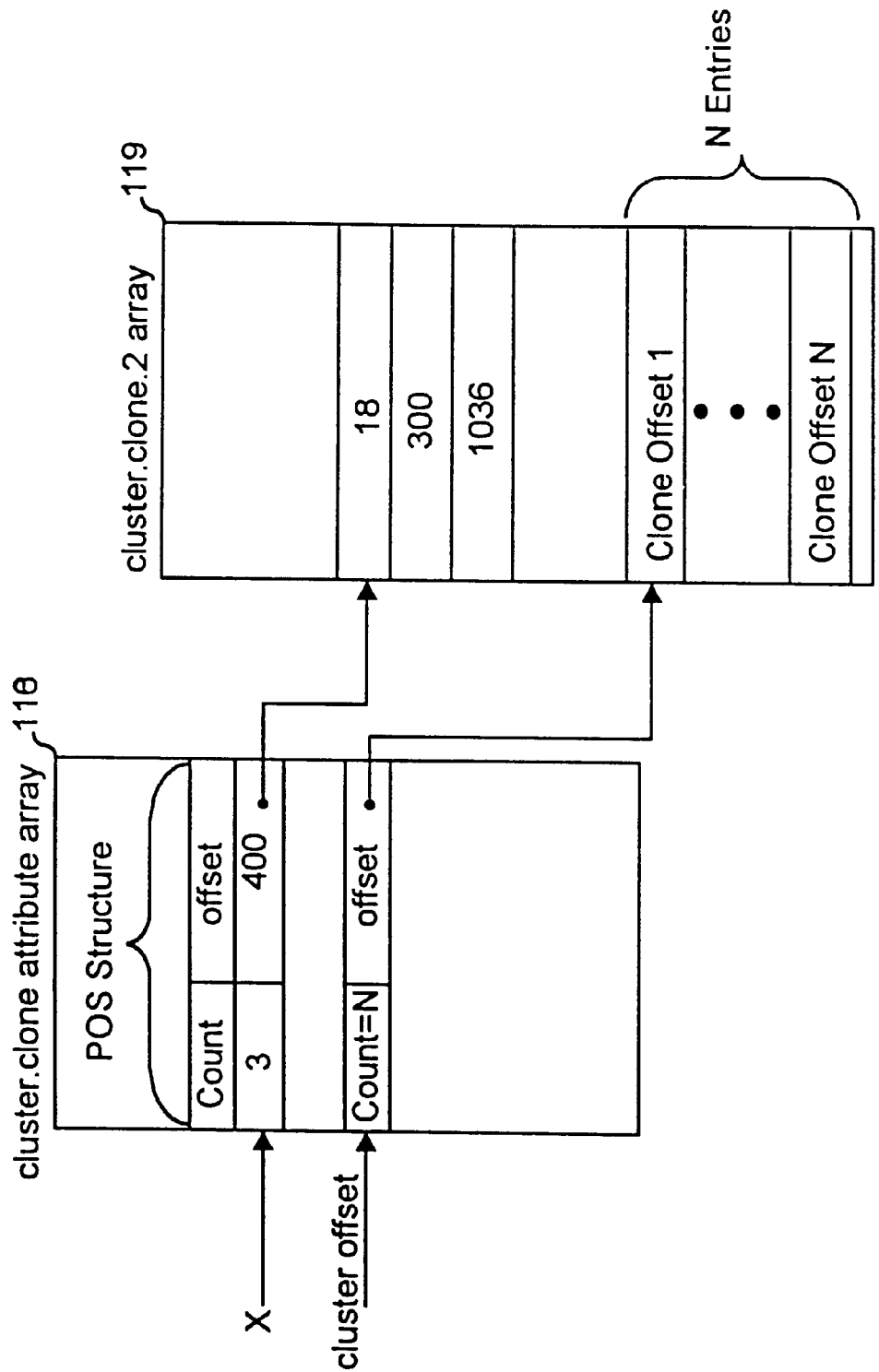
FIG. 3B is a portion of an exemplary cluster entity illustrating use of a POS structure and secondary array to associate a single entry of the cluster entity with multiple clones.

The database allows multiple entries to be associated with a single entry. A POS structure and a secondary array are used to define this many to one relationship. The many to one relationship can be defined for entries in the same or different entities. For example, as shown in FIG. 3B, an attribute array, called cluster.clone 118, uses a POS structure with a secondary attribute array, called cluster.clone.2 119, to associate multiple clone offset values with a single cluster entry. The attribute array, cluster.clone 118, is an array of POS structures and is stored in a file. The secondary attribute array is also stored in a file. The POS structure has two fields: a count and an offset. The count and the offset fields are integers. The count field stores the number of offset values associated with the entry. The offset points to a location in the secondary attribute array where the offset values are stored. In FIG. 3B, a cluster offset called "X" points to a cluster.clone entry having a count of three and a secondary offset of 400. The count indicates that the cluster has three clones. The offset of 400 points to the location in the cluster.clone.2 array 119 that stores a clone offset of 18 that is used to access data from the clone entity. In other words, the offset into the secondary array points to the first associated offset value of a set of offset values, and the count represents the number of offset values in the set. The other two offsets that are used to access the remaining clones of the cluster, offsets 300 and 1036, are stored in consecutive locations in the cluster.clone.2 secondary array 119.

More generally, as shown in FIG. 3B, a count can have any integer value N, and the cluster entry can be associated with N entries of the clone array with N clone offset values.

Alternately, the POS structure with a secondary array is used to store variable length information in which the POS count stores the length of the data and the POS offset points to the starting address of the data.

In another alternate embodiment, the secondary array need not always store offsets into entities but stores actual or absolute data.

In yet another alternative embodiment, the secondary array uses POS structures that have a count and an offset pointing to a tertiary array.

When the modular database is created, the offsets are generated and populated, and the relationships among the data are precompiled. Therefore, the modular database eliminates the need for time consuming table joins. As a result, the database efficiently retrieves data in which a small subset of the entities stored in the database have a disproportionately large amount of data compared to other entities stored in the database.

From another viewpoint, the precompiled offset values stored in the database enable the system to form "limited range" joins, joining the data from two or more tables for a limited (i.e., specified) set of records without having to form full table joins. As a result, when a join is needed that involves the use of data from a very large table (such as the clone entity in the preferred embodiment), the present invention is very efficient because (A) very little memory is needed for the "mini-join" records that are formed compared to the enormous full table joins that would normally have to be formed using conventional relational database management system (RDBMS) technology, (B) very few computational resources are needed to form the mini-join records, since all the offsets needed to retrieve the data for the mini-join have been precomputed and stored in the database.

The entities of the database can be compared to the tables of a relational database. However, the entities of the database comprise a set of separate arrays for each attribute. Unlike in relational databases, instead of having attributes that match between tables, the database has precomputed offsets. Therefore, joins are done on a record-by-record basis, and not on a table basis.

Figure 4:
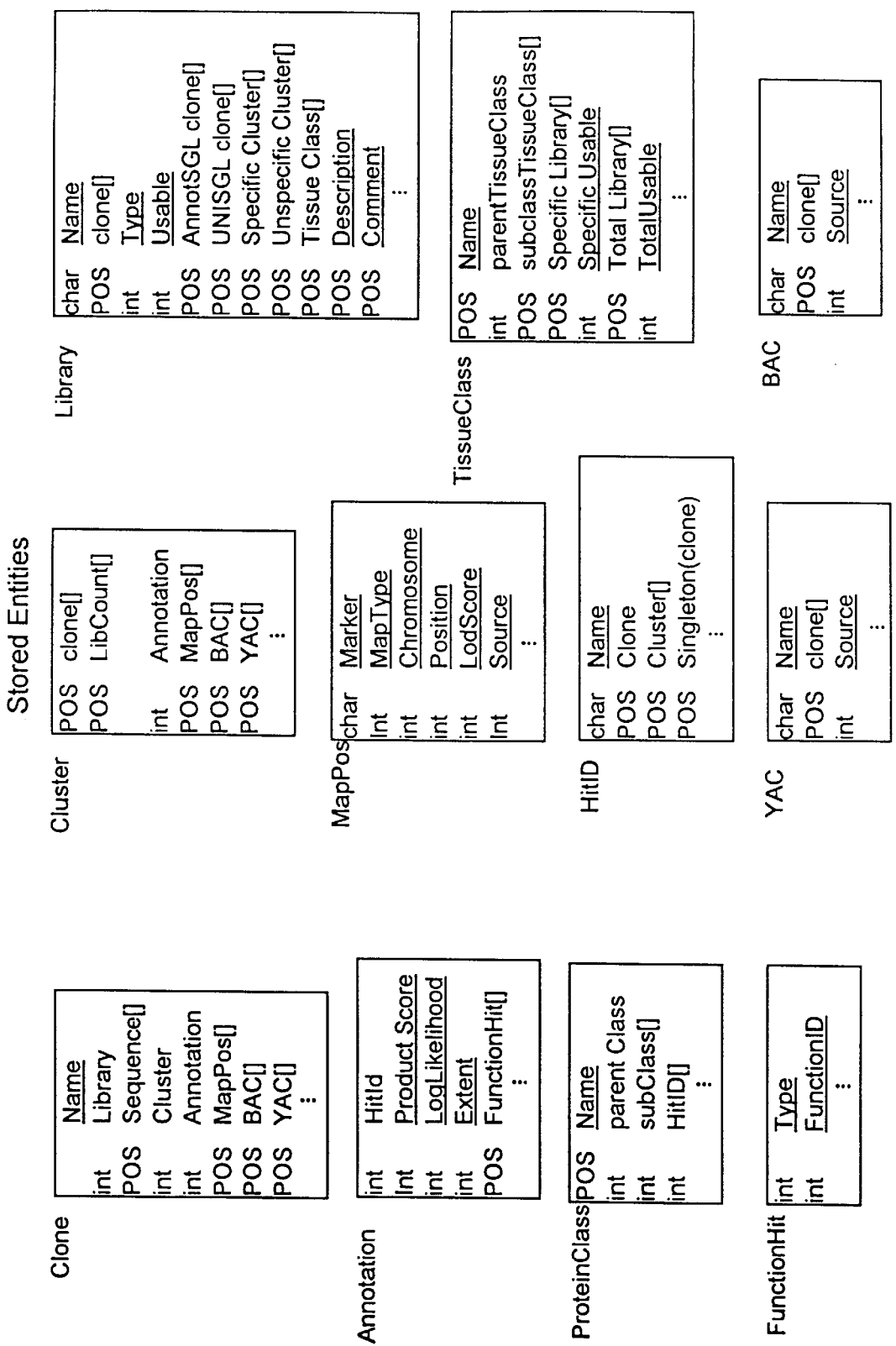
FIG. 4 depicts the logical data structure of the entities of the modular database.

FIG. 4 is a block diagram of the logical structure of the database. Each block is an entity and is labeled with the name of the entity. The attributes are listed inside the block. The underlined attributes represent absolute attribute values. To save storage space, absolute data is generally stored in one entity and other entities store offsets to access the absolute data. Those attributes represented by plain text without underlining represent either an offset or a POS structure. The symbol [ ] indicates that, for a single entry, the attribute can have multiple attribute values, in other words, that the attribute uses the POS structure with a secondary array.

The physical structure of the database is similar to the logical structure. The data type of each attribute is shown next to the attribute's name. The data type is the form in which the attribute is stored within the array. The abbreviations are defined as follows: int means integer and POS means the POS structure described above. Generally "char" means a character string, with certain exceptions. The name attribute in the HitID entity uses a forty-four bit character string. In an alternate embodiment, the name attribute of the HitID entity uses a POS structure. The ProteinClass.name, TissueClass.name, library.comment and library.description attributes use a POS structure to store variable length strings.

For a definition of each attribute, see Table 2.

Procedures

Figure 5:
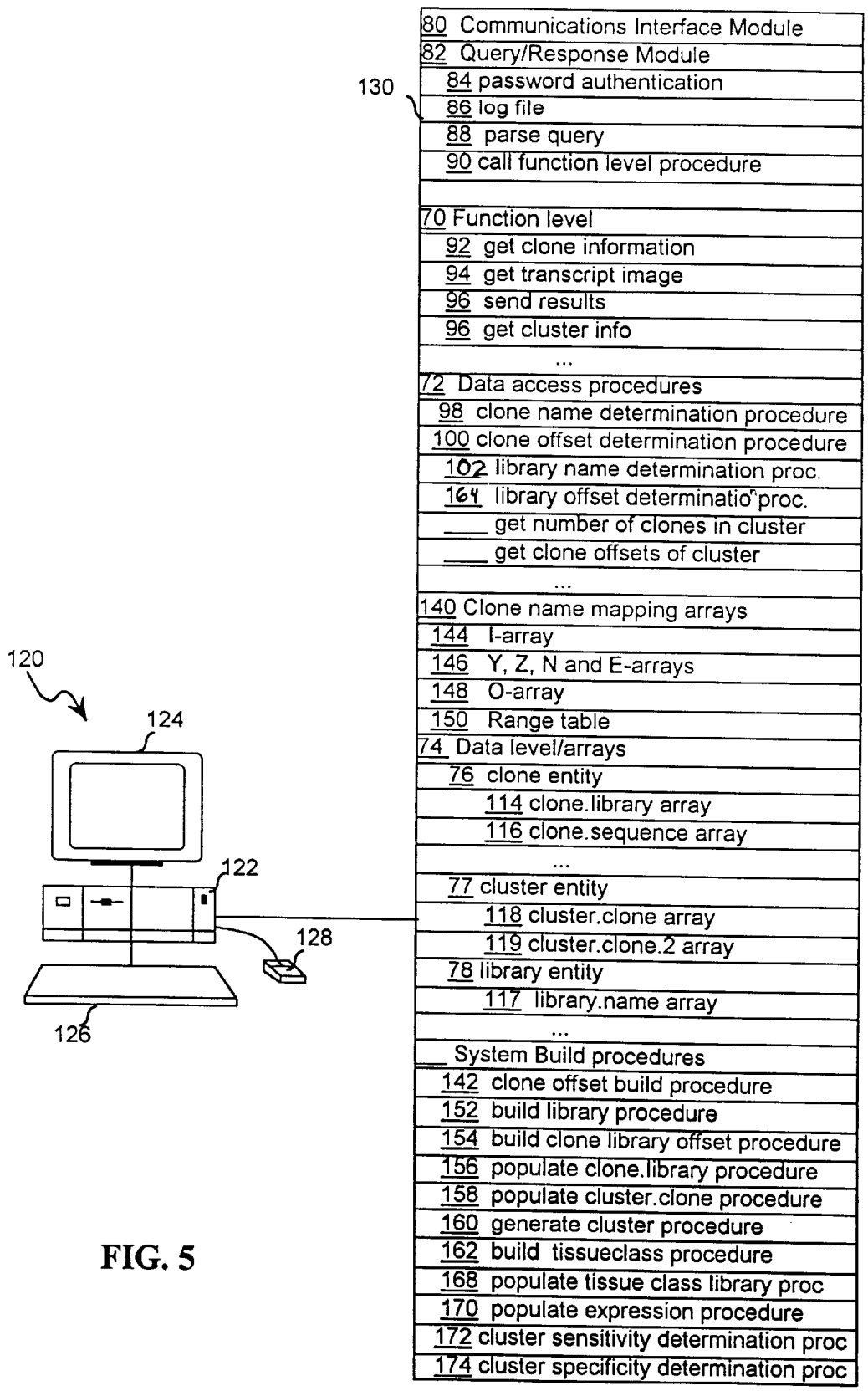
FIG. 5 shows various procedures stored in the memory of the modular database.

FIG. 5 shows an exemplary list of procedures stored in a memory of a computer system 120 of the modular database. This computer system 120 functions as both HTTP server 1 with the LifeSeqAtlas Interface module and the LifeSeqAtlas database server. In an alternate embodiment, two different computer systems perform these functions.

The computer system has a CPU 122, display 124, keyboard 126, mouse 128 and memory 130. The memory 130 may include RAM and various other storage devices such as disk drives. The procedures will be described in more detail below.

Clone Names

In a preferred embodiment, a clone name is not physically stored in the clone entity. Therefore, in FIG. 4, the name attribute of the clone entity does not have a data type. The modular database uses clone name mapping arrays 140 (FIG. 5) which map the clone offset value to the clone name to avoid assigning the same clone offset to different clone names. The clone name mapping arrays are stored in files, and are built each time the modular database is constructed. To build the clone name mapping arrays, clones and the corresponding clone names are collected from many sources. Each source has its own naming convention. For example, clone names begin with certain characters such as I, Y, Z, N and E. The clone names have the format shown in Table 1 below.

TABLE 1

| First Character of Clone Name | Format of Clone Name |
|---|---|
| I | I[number] |
| Y | Y[a . . . 2] [01 . . . 99] [a . . . h] [01 . . . 12] |
| Z | Z[a . . . 23] [01 . . . 99] [a . . . h] [01 . . . 12] |
| N | N[a . . . 23] [01 . . . 99] [a . . . h] [01 . . . 12] |
| E | EST[000001 . . . 999999] |

The nomenclature of the "Y", "N", and "Z" clone names originates from the row and column location of the clone sample which is stored in the form of purified cDNA within a 96-well assay plate. For instance, one clone name format is "Y[letter][plate][row][column]." Not every location of an assay plate may have a "clone," and therefore clone names may not be "consecutive."

The clone names are listed in ASCII files. A clone offset build procedure 142 (FIG. 5) builds the clone name mapping arrays. The clone offset build procedure receives an ASCII file listing all INCYTE clone names and identifies the largest clone number.

Next, the clone offset build procedure creates an "I" array 144 (FIG. 5) for the "I" clone set by allocating sufficient storage in the I-array to store one offset value for every clone number up to the largest identified clone number. The clone offset build procedure populates each entry of the I-array with "−1"s to indicate that the entries are empty. The clone offset build procedure then searches the ASCII file of INCYTE clones and stores a "2" in each entry of the I-array that has an INCYTE clone. For example, if INCYTE clone 1 is in the ASCII file, then a "2" is stored in I-array entry 0. After the I-array is populated with "2"s, the clone offset build procedure sets a clone counter to "0" and searches for "2"s. At the first occurrence of a "2", the "2" is replaced with the clone counter value of "0." The clone counter is then incremented, and the next occurrence of "2" is replaced with the clone counter value of "1". The clone counter is incremented and the process of searching, replacing and incrementing repeats until the end of the I-array is reached. In this way, duplicate clone offset values are avoided.

Note, for example, that the INCYTE clones are numbered sequentially starting with one and not every "number" will actually have a clone. In addition, because INCYTE clone numbers are sequential, the INCYTE clone number will equal the value of the offset into the I-array plus one.

The process described above is also used to generate clone offsets for the non-INCYTE clone names, such as "Y", "Z", "N" and "E." For instance, the "Y" clone names are received in an ASCII file, the maximum number is determined and a Y-array 146 (FIG. 5) is allocated and populated with "−1"s. The Y clone name's in the received ASCII file are not assumed to be sorted in any particular order and the Y-array will typically have unpopulated portions. The Y clones names ASCII file is searched and a "2" is stored in each location of the Y-array having a corresponding Y clone name. The "2"s are replaced in a similar manner to that described above for the I-array. Note that the relationship between a Y-clone name and a Y-array offset is as follows:

Y-array offset=(letter−'a')*9600+(plate−1)*96+(row−'a')*12+(column−1).

Z, N and E arrays 146 are allocated and populated with offsets to clone names in ASCII files using a procedure similar to that just described for the Y array 146.

For the other or "O" type clone names, an O-array 148 (FIG. 5) is allocated based on data from an ASCII file. "O"

type clone names are ordered names and are amenable to binary searching. Therefore, the position of an O type clone name entry in a corresponding O-array equals the O-array offset.

In a preferred embodiment, the range of clone offset values assigned to each of the I, Y, Z, N, E and O arrays is stored by the clone offset build procedure in a range table 150 (FIG. 5) for later use.

Clone Offset Determination Procedure

Figure 6A:
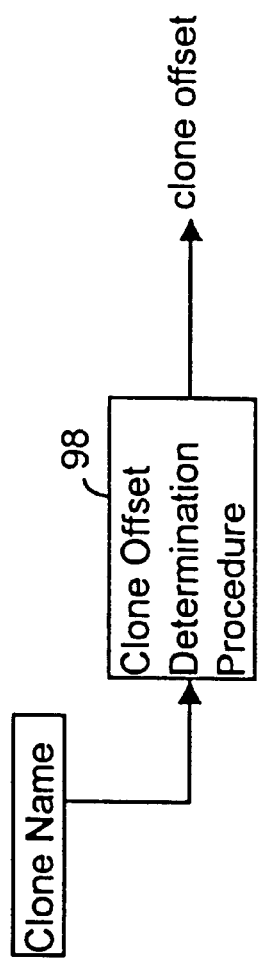
FIG. 6A is a block diagram of a clone offset determination procedure.

The "clone offset" is the offset value used to access all the attributes of a particular clone that are stored in the clone entity. Referring to FIG. 6A, a clone name is passed to the clone offset determination procedure 98 as a parameter, and the clone offset determination procedure 98 returns the clone offset that points to the desired entry in the clone entity. Since a clone name begins with the character indicating which array to use, such as an "I" or "Y", the appropriate array can be identified quickly. For an INCYTE clone, since the I-array offset equals the INCYTE clone number minus one, the clone offset determination procedure subtracts a one from the clone number to generate the I-array offset. The clone offset determination procedure then uses the generated I-array offset to access the clone offset value stored in the I-array and returns that clone offset value.

For a name beginning with "Y," the clone offset determination procedure determines the Y-array offset using the following equation:

$$\text{Y-array offset} = (\text{letter}-`a`)*9600+(\text{plate}-1)*96+(\text{row}-`a`)*12+(\text{column}-1).$$

The clone offset determination procedure uses then uses the Y-array offset to access the location storing the clone offset value in the Y-array and returns that clone offset value. The clone offsets for the "Z," "N" and "E" type clone names are determined in a manner similar to that for the "Y" clones.

For a clone name beginning with "O", the clone offset determination procedure searches the O-array for the clone name and the position of the clone name within the O-array indicates its O-array offset value. Since the clone offset build procedure stored the minimum value of the clone offset of the O-array in the range table, the clone offset determination procedure adds the O-array offset value to the minimum value of the clone offset in the O-array to generate the clone offset.

Clone Name Determination Procedure

Figure 6B:
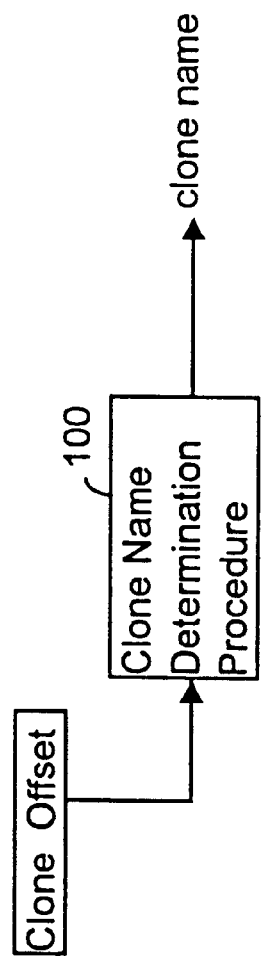
FIG. 6B is a block diagram of a clone name determination procedure.

Referring to FIG. 6B, a clone offset is passed as a parameter to the clone name determination procedure 100, which returns the corresponding clone name. The clone name determination procedure 100 determines which array stores that clone offset from the value of the clone offset and the range table of clone offset values for the I, Y, Z, N, E and O arrays.

For clone offset values in the I-array, the clone name determination procedure calculates the clone name as the clone offset plus one. For clone offset values in the Y, Z, N and E arrays, the clone name determination procedure searches the appropriate mapping array for the stored clone offset value and determines the corresponding array offset from the position of the clone offset value within the mapping array. The clone name determination procedure then applies an inverse function to that used to map that clone name to the array-index value to generate the clone name.

For clone offset values in the O-array, the clone name determination procedure subtracts the minimum O-array clone offset value from the clone offset to determine the O-array offset value. The clone name determination procedure uses the O-array offset value to access the clone name stored at that O-array offset. The clone name determination procedure then returns the clone name.

Building the Modular Database

The modular database is populated with biomolecular information. An example of populating each of three types of attributes used in the database will be provided. Similar types of attributes will be populated in a similar manner.

Populating "Absolute" or Actual Attributes

As an example of populating entries of an entity with absolute data, the population of the library.name, library.type and library.usable attribute arrays will be described. The library "type" attribute is an integer and represents a library preparation procedure. The library "Usable" attribute is also an integer and represents the number of usable clones in a library.

An ASCII file storing library names with the type and usable information is provided. A library build procedure 152 (FIG. 5) sorts the ASCII file by library name, counts the number of entries in the ASCII file, and allocates space for the library.name, the library.type and the library.usable attribute arrays. Beginning with the first entry, library.name [0], the library names from the ASCII file are stored sequentially in the library.name array. The position of the library name within the library.name array corresponds to its library offset value. After a library name has been stored within the library.name attribute array, its corresponding type and usable attributes are stored in the type and usable attribute arrays.

Populating Direct Offset Attributes

As an example of populating entries with direct offset data, the population of the clone.library attribute array will be described. The clone.library attribute array is an array of integers that are offsets pointing to an associated entry in the library array. A build clone library offset procedure 154 (FIG. 5) populates the clone.library attribute array with the corresponding library offset values.

After the build clone library offset procedure 154 populates the library.name attribute array thereby assigning library offsets to each library name, a populate clone.library procedure 156 (FIG. 5) updates the clone.library attribute array of the clone entity. An ASCII file mapping the clone names to a library name is provided. For each clone name in the ASCII file, the populate clone.library procedure calls the clone name determination procedure using the clone name to determine the clone offset value. The populate clone.library procedure also calls a library offset determination procedure passing the library name to determine the library offset value. The populate clone.library procedure stores the library offset in the corresponding clone.library attribute array at the clone offset value. In other words, clone.library [clone offset]=library offset.

Populating a POS Array

As an example of populating entries of an entity using a POS structure, the population of the cluster.clone attribute array will be described with reference to FIG. 7.

Figure 7:
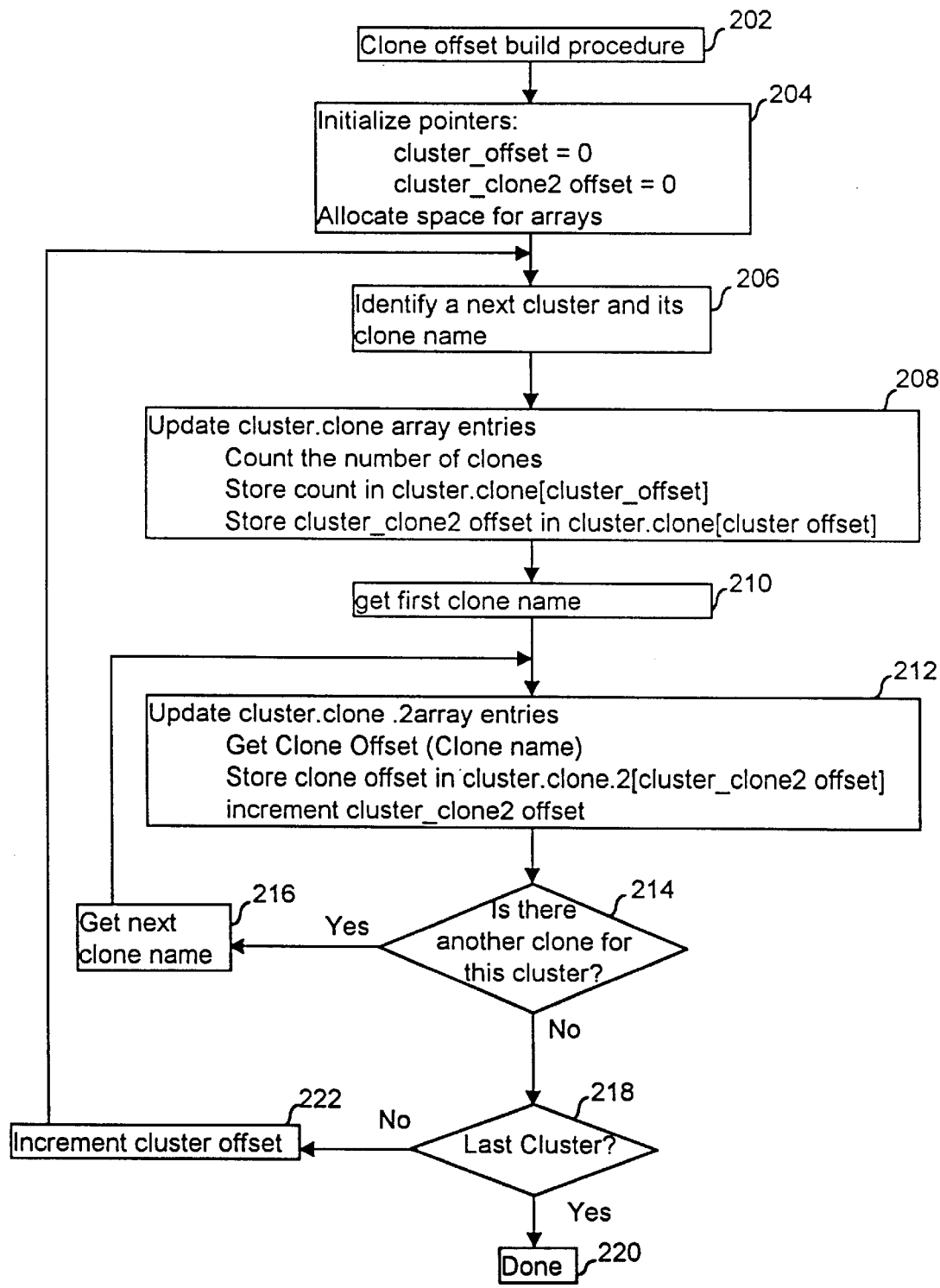
FIG. 7 is a flowchart showing a method of populating the POS structure of FIG. 3B to associate a single entry of a cluster entity with multiple clones.

In FIG. 7, a populate cluster.clone procedure 158 (FIG. 5) populates the cluster.clone and the cluster.clone.2 attribute arrays shown in FIGS. 3B and 4. An ASCII file mapping the clone names to a cluster is provided. In step 202, the clone offset build procedure builds the clone offset values. In step 204, a cluster_offset and cluster_clone2 offset are initialized to zero to point to the first entry of the cluster.clone and cluster.clone2 secondary arrays, respectively. The populate cluster.clone procedure identifies the total number of clusters and clones in the ASCII file. The populate cluster.clone procedure creates an empty cluster.clone array of POS structure whose size is based on the total number of clusters in the ASCII file. The populate cluster.clone procedure also creates an empty secondary array, cluster.clone.2, whose size is based on the number of total number of clones identified in the ASCII file.

In step 206, the populate cluster.clone procedure reads the ASCII file and identifies a first cluster (or next cluster, if this is not the first cluster being processed). In step 208, the cluster.clone array is accessed by the cluster_offset. The populate cluster.clone procedure counts the number of clone names in the first cluster from the ASCII file and stores the count in the count field of the cluster.clone array at the cluster_offset position. The populate cluster.clone procedure stores the offset for the next unused slot in the cluster_clone2 array in the POS structure of the cluster.clone array at the position designated by the value of cluster_offset.

In step 210, the populate cluster.clone procedure populates the cluster.clone.2 array with the corresponding clone offset values. In step 212, the populate cluster.clone procedure calls GetCloneOffset function for the Clone name, and stores the returned clone offset value in the cluster.clone.2 array at the position pointed to by the cluster_clone2 offset, and increments the cluster_clone2 offset. Step 214 determines if there is another clone for this cluster. If so, in step 216, the populate cluster.clone procedure gets the next clone name and repeats the process at step 212 for the next clone name. If not, in step 218, the populate cluster.clone procedure determines if there are more clusters. If not, the process ends (220). If so, in step 222, the populate cluster.clone procedure increments cluster_offset and proceeds to step 206 to repeat the process for the next cluster Building the Database A system build procedure calls various build procedures to build portions of the database. In particular, attributes such as those storing offset values are populated as the offset information becomes available.

Certain procedures are executed before other procedures. For instance, the clone offset build-procedure is executed to build the clone name mapping arrays. After executing the clone offset build procedure, the library build procedure and the populate cluster.clone procedure are executed. Additional build procedures, similar to the procedures described above, are called to build and populate attributes of other entities.

Entity Name and Offset Determination Procedures

Often the name attribute of a entity is used to uniquely designate an entry of interest. Therefore, an exemplary library offset determination procedure 164 (FIG. 5) will also be described. The parameters and output of the library offset determination procedure are similar to those shown in FIG. 6A. A particular library name is passed as a parameter, and the library offset determination procedure returns the library offset value that points to the particular entry storing that library name in the library.name attribute array of the library entity.

To determine the corresponding library offset for the particular library name, the library offset determination procedure searches the library.name attribute array for the particular library name. Since the names are ordered the search is fast. The position of the library name within the library.name attribute array corresponds to the library offset value for the particular library name.

A library name determination procedure 102 (FIG. 5) is also provided. The parameters and output of the library name determination procedure are similar to those shown in FIG. 6B. A particular library offset is passed as a parameter, and the library name determination procedure returns the library name. The procedure uses the particular library offset to directly access the particular library name stored in the library.name attribute array.

Although the system has been described with respect to certain attributes of the clone, cluster and library entities, these descriptions apply to populating and accessing the remaining attributes of clone, cluster, library and the other entities. Preferably, for those entities and attributes sharing similar data types, generalized functions are used to access the data stored in those entities. For example, since the ProteinClass, TissueClass, BAC, YAC and HitID entities all have a name like the library entity, a general function, such as FindOffset(entity, name) and FindName(entity, offset), are provided for those entities. The FindOffset and FindName functions are similar to the library name determination procedure and the library offset determination procedure except for passing an additional parameter to specify the entity.

Because offsets are used to point to the information for a desired entity, the biomolecular database can be modified easily without disturbing other entries. In particular, additional attributes are added to an entity by generating an additional attribute array of the desired data type, ordered appropriately with respect to the current offsets for the entries for that entity, and storing the new attribute array in a file. New database access procedures are provided to access the data stored in the new attribute array.

Clustering Techniques

The individual sequences stored in the clone entity represent fragments of a gene. Prior to populating the modular database, a generate cluster procedure 160 (FIG. 5) groups the sequences into clusters and these clusters are stored in the cluster entity. Clustering techniques assess the homology arid overlap of pairs of nucleotide sequences from both internal and the public domain databases. Sequences are assigned to a cluster based on sequence homology when the homology satisfies the specific criteria for overlap with respect to other sequences in the database. Each cluster represents a specific gene and will be annotated with a designation assigned to a representative sequence match with an annotated entry from GenBank. This annotation information is stored in the annotation entity.

The present invention provides an improved clustering technique that clusters contiguous cDNA species, each having about 100–500 base pairs, such that much longer cluster sequences are obtained which may encompass a full length gene.

To cluster the clones, a generate cluster procedure 160 (FIG. 5), first executes BLAST to compare all sequences in an internal database, such as the INCYTE clones. Query and database sequences are input to BLAST. BLAST compares the query and database sequence pairs using a scoring system, and outputs pairs of sequences called High-scoring Segment Pairs (HSP). An HSP has two sequence fragments of arbitrary length whose alignment is locally maximal and for which an alignment score meets or exceeds a threshold or cutoff score. In the implementations of the BLAST algorithm described herein, each HSP includes a segment from the query sequence and a segment from a database sequence.

Multiple HSPs involving the query sequence and a single database sequence may be statistically treated in a variety of ways. By default, the programs use "Sum" statistics. Therefore, the statistical significance ascribed to a set of HSPs may be higher than that ascribed to any individual member of the set. When the assigned significance satisfies the specific threshold (E parameter), a match will be reported to the user.

The BLAST parameter E establishes a statistical significance threshold for outputting database sequence matches. E represents an upper boundary of the expected frequency of random occurrence of an HSP or set of HSPs within the context of the entire database search. In the implementations of the BLAST algorithm described herein, $E=10^{-5}$.

The context of the BLAST comparison includes the length and residue composition of the query sequence, the length of the database, a fixed hypothetical residue composition for the database, and the scoring system. Each nucleotide in a sequence is represented by a character. The significance of an alignment score depends on the specific scoring matrix employed and the length and composition of the query sequence and database, all of which may vary with each search. For the purpose of calculating significance levels, Y is the effective length of the query sequence and Z is the effective length of the database. The default values for Y and Z are the actual lengths of the query and database sequences, respectively. To normalize the reported statistics when searching databases of different lengths, Z may be set to a constant value for all database searches. In the implementation described herein, $Z=3\times10^9$. Similarly, when querying with sequences of different lengths, Y can be used to normalize over all searches.

Figure 8A:
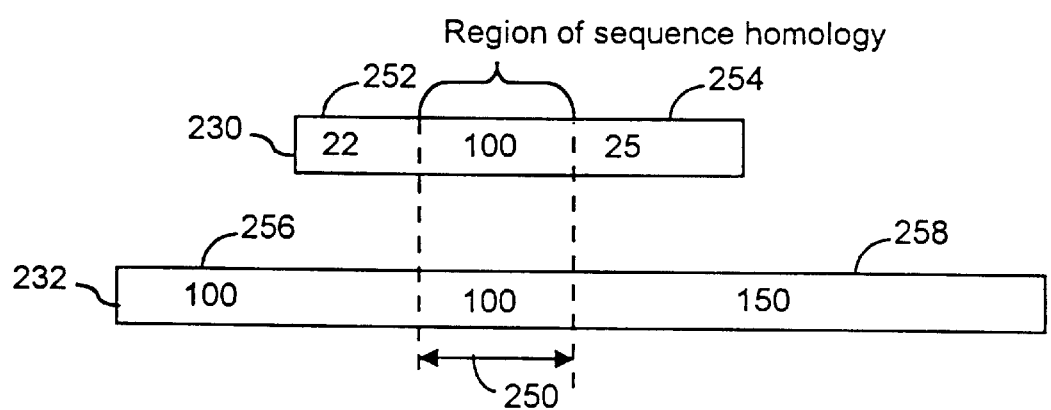
FIG. 8A shows exemplary sequences suitable for use with the clustering method of FIG. 8B.

FIG. 8A shows an HSP of two sequences 230 and 232 from the BLAST results. The region of homology 250 between the sequences 230 and 232 has 100 nucleotides. There are four adjacent non-matching regions 252, 254, 256, and 258, each having 22, 25, 100 and 150 nucleotides, respectively.

Figure 8B:
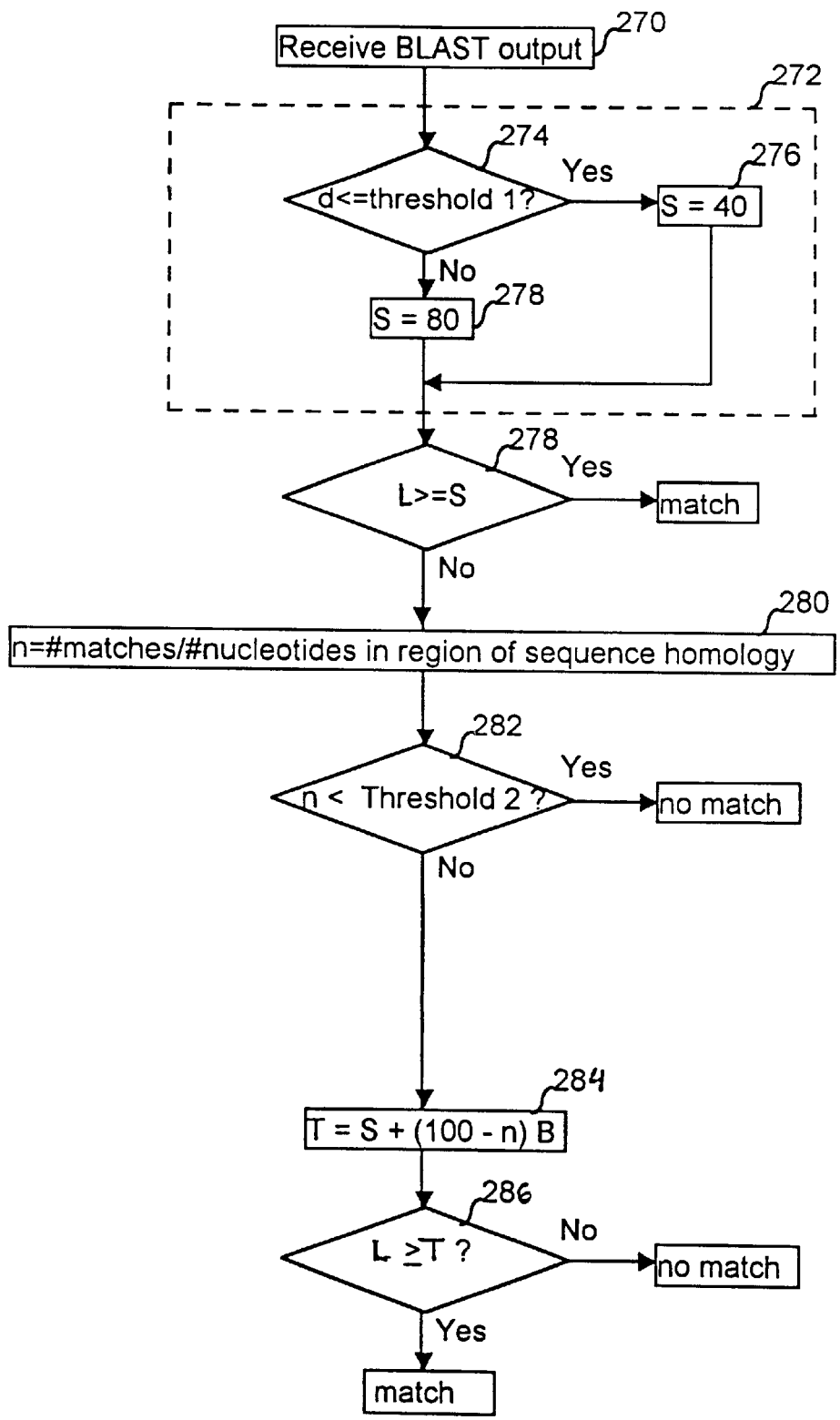
FIG. 8B is a flowchart of an improved clustering method of the present invention.

In FIG. 8B, the generate cluster procedure further filters the BLAST results to form additional clusters. Referring also to FIG. 8A, the filter uses the following parameters:

L—The length of the region of sequence homology 250; in FIG. 8A, L equals 100, n—An integer representing the percent of matching bases or nucleotides within the region of sequence homology 250. The value of n ranges from zero to one hundred.

d—The length of the shortest non-matching sequence adjacent the region of sequence homology. In FIG. 8A, region 252 is the shortest non-matching sequence adjacent the region of sequence homology, therefore d equals twenty-two.

Referring to FIG. 8B, in step 270, the BLAST output is received. Block 272 sets a parameter called S in steps, 274, 276 and 278. S represents a number of bases and is a function of d as defined above. S is equal to either a first value or a second value depending on whether the region of sequence homology is in the middle or at the end of the sequence. Step 272 determines if the region of sequence homology is in the middle or at one of the ends of the sequence by comparing the length of the shortest non-matching sequence adjacent the region of sequence homology d to a first predetermined threshold value, threshold 1. In one embodiment, the first predetermined threshold value equals five. If d is less than or equal to five, then in step 274 S is set to a first value such as forty. If d is greater than the first predetermined threshold value, step 276 sets S to a second value such as eighty.

In step 278, the length of the region of sequence homology L is compared to S. If L is greater than or equal to S, then the sequences match. If L is less than S, then other parameters are considered. Step 280 calculates n, the number of nucleotide matches between the pairs in the region of sequence homology divided by L.

Step 282 compares n to a second threshold value, threshold 2. In one embodiment, the second threshold value equals 95 (representing a 95% match threshold). If n is less than the second threshold value, then there is no match. If n is greater than or equal to the second threshold value, step 284 calculates T, a variable threshold that is used to determine if a match occurred. T is determined using the following relationship:

$$T=S+(100-n)B.$$

In one embodiment, B is a predetermined constant representing an incremental number of nucleotides required for a match, such as two. Therefore for every one percent difference between 100 and n, two additional nucleotides are required for a match. Alternately, B is a function of d, the length of the shortest non-matching sequence adjacent the region of sequence homology.

Step 286 compares L to T:

If $L \geq T$ the filter indicates a "match,"

if $L < T$, the filter indicates "no match."

After filtering as described above, the generate cluster procedure further evaluates the pairs of sequences to establish clusters. The sequences include sequences from INCYTE and public domain databases, 'template' sequences which are assemblies of ESTs or other sequences and 'anchoring' sequences which are sequences from public domain databases with a functional annotation. Anchoring sequences are compared using sequence comparison programs such as BLAST, BLAST2, FASTA, and CrossMatch or other implementations of Smith-Waterman to the complete set of sequences in the database. Sequences are assembled with a sequence assembler such as Phrap (Green, P., Univ. of Washington), ClustalW (Thompson, J. D. et al. (1994) Nucleic Acids Res., 22:4673–4680) GCG Assembly (Genetics Computer, Inc.), or CAP (Huang, X. (1996) Genomics 33: 21–31), to derive sets of template sequences representing 'pre-clusters'. The results of this comparison include clusters attached to anchoring sequences, template sequences for previous clusters and singletons which did not cluster.

The sequences derived from the comparison above are further compared to each other using one of the sequence comparison tools discussed above. For instance, BLAST is used with the parameter Z equal to $3\times10^9$ and E equal to $10^5$. The sequence comparison maintains a record of each query sequence, including the query sequence identification (ID), query length, hit(s) sequence identification, hit(s) length, and the highest score derived from the comparison. This comparison results in groups of pre-clustered sequences and singletons with 5' hits. Lists are kept of duplicate clones and sequence IDs, the duplicates are removed, and the BLAST results are filtered.

The groups of sequences are further characterized to avoid inappropriately associating sequences by considering the specific context of each sequence match. For instance, considering the sequence context prevents clustering of 5' and 3' sequences which belong to different clones, and also prevents merging clusters with common sequences but known to be different genes by applying more stringent criteria to the evaluation of the match. Sequences which have matches at the 5' ends of clones are clustered, and sequences with matches at 3' ends are excluded. The remaining singletons and 3' clusters are examined. If the specific clone sequence represented by a 3' cluster or singleton forms a match with a single 5' cluster it will be merged with that cluster. Cluster annotations and sequence composition are modified to reflect any changes that occur and files are generated to track all changes.

The generate cluster procedure also generates a log during the clustering process. The log lists the order in which operations were performed and the changes that occurred such as the number of new clusters generated, the number of clones contained within the new clusters, the number of singletons incorporated into clusters, the number of singletons eliminated, and the number of merged clusters.

Transcript Imaging

The modular database allows for systematic and quantitative characterization of the distribution of ESTs or clones in a plurality of cDNA libraries. Transcript imaging compares expression data with mapping information and annotation at the genome level, rather than one gene at a time, and validates the quality of the clustering of the clones of the cDNA libraries. In particular, in the database, the cluster entity has an Annotation attribute that associates clusters with annotation information.

Transcript imaging is based on the analysis of the expression of a cluster, rather than expression of individual clones or sequences, and on the analysis of cluster expression in the cDNA libraries with respect to tissue type.

In the modular database, the libraries are associated with tissue classes, and the tissue classes are hierarchically organized. The hierarchy tree of tissue classes is stored in the TissueClass entity. In the TissueClass entity, each tissue class name is stored in the name field of the TissueClass.Name attribute array. In the hierarchy, tissue classes are associated with a parent tissue class and a sub-class tissue class using TissueClass.ParentTissueClass and TissueClass.subclassTissueClass attribute arrays, respectively. Each library is associated with at least one tissue class in the hierarchy.

The hierarchy "tree" of tissue classes is based on the 1998 Medical Subject Headings (MeSH™) available from National Library of Medicine. The top level of tissue classes is system based and includes the following classes: cardiovascular system, cells; digestive system; embryonic structures; endocrine system; genitalia, female; genitalia, male; hemic and immune system; musculoskeletal system; nervous system; respiratory system, sense organs, stomatognathic system; tissue types; and urinary tract. The lower level of tissue classes are tissue specific and include blood vessels, heart, blood cells, bone marrow cells, cultured cells, connective tissue cells, epithelial cells, islets of Langerhans, neuroglia, neurons, phagocytes, biliary tract, esophagus, gastrointestinal system, liver, pancreas, fetus, placenta, chromaffin system, endocrine glands, neurosecretory systems, ovary, uterus, penis, prostate, seminal vesicles, testis, bone marrow, immune system, cartilage, muscles, skeleton, central nervous system, ganglia, neuroglia, neurosecretory system, peripheral nervous system, bronchus, larynx, lung, nose, pleurus, ear, eye, nose, mouth, pharynx, connective tissue, epithelium, exocrine glands, bladder, kidney and ureter. Some of these second level categories are linked to more than one first category level. First level headings and second level headings are coded using the MeSH™ code system. Specific libraries are then subdivided between one or more of the second level categories.

For example, clones isolated from a fetal heart sample library belong to multiple tissue classes. Within the tissue class entity, many tissue class entries have a name of "heart". The entry of the library entity for the fetal heart sample library would be associated with or point to at least one tissue class entry in the tissue class entity having a tissue class name of "heart." The fetal heart sample library entity would be associated with those tissue classes entries having a name of "heart" and having a parent tissue class called "embryonic structures" or "cardiovascular system."

When the modular database is created, a build TissueClass procedure 162 (FIG. 5) populates the TissueClass.Name attribute array with the tissue class names. The build TissueClass procedure also populates the TissueClass.ParentTissueClass and TissueClass.subclassTissueClass arrays with offsets that define the hierarchy tree of tissue classes. The relationship between tissue class names, parent and subclasses is predefined and supplied to the build TissueClass procedure in a file. Next, a populate TissueClassLibrary procedure 168 (FIG. 5) populates the TissueClass.SpecificLibrary attribute array with the corresponding library data using the methods described above.

Using the hierarchical tissue classes of the database, clusters can be examined to determine a specificity of expression of the clusters with respect to the libraries and tissue classes. To determine the specificity of expression, clusters whose members, or clones, are expressed in a single library are identified. If there is no library specificity, then clusters whose clones are expressed in a single tissue class are identified. A cluster may be fully tissue class specific for more than one tissue class because of the overlapping nature of the tissue classes. If a cluster is not tissue class specific, clusters that are partially tissue class specific are identified. A cluster is partially tissue class specific if a certain fraction of its clones are derived from libraries that are in the same tissue class. This fraction is called a threshold specificity score.

The library entity has Library.SpecificCluster and Library.UnspecificCluster attribute arrays that associate clusters with the entries of the library entity based on their cluster specificities as described above.

If a cluster is found to be specific for a library or class, several values are provided based on the data stored in the modular database:

1. an expression level (E)
2. a sensitivity, and
3. a cluster specificity value.

The expression level (E) is calculated in a calculate expression level procedure 170 (FIG. 5). The expression level represents the number of clones in a cluster (N) expressed in a particular library divided by the number of clones (P) in that library, as in the following relationship:

$$E=N/P.$$

In the modular database, the number of clones in a cluster (N) is stored in the POS structure of the Cluster.Clone attribute array. The number of sequences in each library is stored in the library.Usable attribute array.

The sensitivity is also calculated, in a cluster sensitivity determination procedure 172 (FIG. 5), by dividing the number of clones in a cluster (N) by the total number of sequences (Q) of all the libraries in a tissue class, so that S=N/Q. For example, the number of clones in a cluster (N) is retrieved from the Cluster.Clone attribute array as described above. The cluster.LibCount attribute associates various libraries with the cluster. The libraries are associated with tissue classes using the Library.TissueClass attribute. For a particular tissue class, the number of sequences (Q) in that tissue class is retrieved from the TissueClass.TotalUsable attribute array. The cluster specificity value or threshold specificity score is calculated for each cluster in a cluster specificity determination procedure 174 (FIG. 5). A cluster is reported to be library specific if 75% or more of the clones in the cluster are expressed in a library of interest. Partial specificities are reported for clusters when less than 75% of the clones in the cluster are expressed in the library of interest. Alternately, partial class specificity is reported when less than 75% of the clones in the cluster are expressed in the tissue class of interest. In one embodiment, the cluster specificity determination procedure identifies the clones from the Cluster.Clone attribute array, accesses the clone.library attribute array, counts the number of clones associated with each library and divides the largest count by the total number of clones in the cluster to generate the cluster specificity value.

Similar to the hierarchy of Tissue Classes, as shown in FIG. 4, a ProteinClass entity provides a hierarchy of proteins using the parent-subclass organization described above. The ProteinClass entity is associated with the HitID entity which associates clusters with HitID entries. Therefore, clusters can be analyzed by ProteinClass.

Clusters, via the Annotation entity, are associated with protein functions stored in the FunctionHit entity. Therefore, clusters can also be analyzed by protein function.

In another alternative embodiment, a biomolecular entity provides a hierarchy of biomolecules using the parent-subclass organization described above.

Mapping

The modular database also provides a way to store and associate mapping information with clones and clusters. Referring back to FIG. 4, a MapPos entity stores mapping information that is supplied from multiple public domain databases such as the Stanford Human Genome Center (SHGC) and the Whitehead Institute Center for Genome Research (WICGR). The clone and cluster entities each have POS structures that associate the entries of the MapPos entity with the entries of the clone and cluster entities.

The MapPos entity is populated in a manner similar to the procedures described above. To populate the MapPos entity, a file of clone names with the mapping information is supplied to a populate map information procedure. The populate map information procedure populates entries of the MapPos entity with the mapping information and also populates the clone.MapPos attribute of the clone entity. After the clone entity is populated with the mapping information, the populate map information procedure populates the cluster.MapPos attribute of the cluster entity for those clusters that have clones that are mapped.

In an alternate embodiment, the populate map information procedure applies a filter before associating a cluster entry with the MapPos entity. For instance, this procedure checks that all clones making up a particular cluster are mapped to the same MapPos entity before associating that particular cluster with an entry of the MapPos entity.

Similar to the procedures described above, a get map info procedure retrieves the mapping information from the MapPos entity using an offset into the MapPos entity. Therefore, mapping information from many sources is combined into a single database. Using this database, statistical analysis of the mapped clones in clusters can be performed.

In this way, no table joins are performed because the relationships among the data are precompiled.

Although the invention was described using a database for sequence data, the database can also be used with other biomolecular information. For example, the invention can store full length mRNA sequences, genomic sequences, synthetic sequences, peptide sequences, polypeptide sequences, peptide nucleic acid sequences, and genome mapping, pharmacogenomic, proteomic, single nucleotide polymorphism, genotyping and forensic data.

TABLE 2

Entity Description

Clone Entity name - derived from clone offset to clone entity table
library - offset to library entity associated with the clone name
sequence - array of offsets (POS structure) for clone nucleic acid sequence
cluster - offset to cluster entity containing clone
annotation - offset to annotation entity
MapPos - array of offsets to MapPos Entity
BAC - array of offsets to BAC entity for associated Bacterial artificial chromosome clones
YAC - array of offsets to YAC entity for associated Yeast artificial chromosome clones Cluster Entity Clone - is a POS structure to indicate the clones belongs to a particular cluster
LibCount - stores a POS structure and is used to indicate the number of libraries in which that cluster appears, and the associated offset values of the entries of the library antedate in which that cluster appears.
Annotation - offset to the Annotation entity
MapPos - is POS structure for associating mapping information with a cluster.
BAC - array of offsets to BAC entity for associated Bacterial artificial chromosome.
YAC - array of offsets to YAC entity for associated Yeast artificial chromosome Library Entity Name - the library name
Clone - a POS structure for associating multiple clones with a library
Type - a number representing library preparation condition
Usable - number of usable clones in library
AnnotSGL clone[ ] - POS structure for associating annotated singleton (a cluster consisting of one clone) clones with Cluster names that are identical to their Clone name
UNISGL clone [ ] - POS structure for associating unique singleton clones with cluster name
Specific Cluster - array of offsets to cluster entity, for those clusters that occur in a single library or class
Unspecific Cluster - array of offsets to cluster entity for those clusters that occur in multiple libraries or tissue classes
Tissue Class - array of offsets into TissueClass entity to associate a library with tissue classes
Description - uses a POS structure to store variable length data stored in a secondary file. The description information describes the tissue pathology.
Comment - similar to description and uses a POS structure to store variable length data stored in a secondary file.

Annotation Entity

HitID - an offset pointing to the HitID Entity
Product Score - an integer representing a normalized value between 0 and 100 indicating the strength of a BLAST match between two sequences.
LogLikelihood - an integer representing the probability that a sequence match was due to random chance.
Extent - an integer which indicates whether any coding information is present within the clone.
FunctionHit - uses a POS structure to point to multiple entries in the FunctionHit Entity. Function Hit means protein function and is taken from the annotation.

TissueClass Entity

Name: uses a POS structure to store a name having any number of characters
parent tissue class: is an offset pointing to another entry in the TissueClass table that is the parent tissue of the tissue in the Name attribute. (such as if name is "leucocyte", then the parent would be the tissue class having a name attribute equal to "blood.")
subclass TissueClass: since a tissue class can have many subclasses, a POS structure points to the starting entry a secondary array or file. The information stored in the secondary array or file is actually another offset pointing to another entity in the Tissue TABLE 2-continued Entity Description Class. If there are no subclasses, the POS structure stores a 0
in its number or count.
Specific library[ ] - an array of offsets pointing to the library entity that is
specific for the cluster
Specific Usable - an integer meaning the number of clones in the
library(ies) that the cluster is specific to
Total Library [ ] - an array of offsets pointing to total number of usable
clones in the library(ies) a clone is specific to
Total Usable - an integer meaning the total number of usable clones in
library(ies) a cluster is specific to MapPos Entity Marker - A unique positional identifier for a chromosomal location
MapType - an annotation specifying the type of map
Chromosome - an integer specifying the chromosome
Position - an integer indicating a location on a chromosome
LodScore - an integer representing a ratio of likelihood of being within
a location on a chromosome
Source - an integer indicating the map source ProteinClass Entity Name has a variable length and uses a POS structure.
parentClass - an offset pointing to a higher protein function class
subClass - an offset pointing to a protein function subclass
HitID - an array of offsets to the HitID entity HitID Entity Name is a GenBank internal identifier that is associated with a
homolog which is used to access data in GenBank.
Clone - an offset into the clone entity
Cluster - an array of offsets to the cluster entity
Singleton - an offset into the clone entity FunctionHit Entity Type - an integer representing a protein function class
FunctionID - an integer identifying a protein function derived from
annotation YAC Entity Name is an identifier for the YAC
clone - an array of offsets to the clone table associated with a YAC
clone
Source - an integer representing the source of the YAC BAC Entity Name is an identifier for the BAC
clone - an array of offsets to the clone table associated with a BAC
clone
Source - an integer representing the source of the BAC While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A method of storing biomolecular data in a database, comprising:

generating a set of entities, each entity storing attributes for a plurality of entries, at least one attribute being stored in an array wherein data associated with an entry is stored at a location in the array, an entity offset designating the location of the data associated with each entry within the array, wherein the same entity offset is used to access data associated with a particular entry for all attributes within the entity; and storing the generated set of entities in a memory.

2. The method of claim 1, wherein at least one entity is a clone entity having a clone name attribute associated with a clone name, further comprising:

generating the clone name attribute as a function of the entity offset of the clone entity.

3. The method of claim 1, wherein at least one entity has a first attribute, further comprising:

generating the first attribute value based on the associated entity offset.

4. The method of claim 1, wherein the set of attributes includes a first entity and a second entity, and further comprising:

storing a particular offset value associated with a particular entry of the second entity in the a first array for an entry of the first entity.

5. The method of claim 1, wherein the set of entities includes a clone entity and a library entity, and further comprising:

storing a particular library offset value associated with a particular library entity entry of the library entity in a clone library array for a clone entry of the clone entity.

6. The method of claim 1, wherein the set of entities includes:

a first entity with a plurality of first entries in a first array, and a second entity with a plurality of second entries in a second array, one of the plurality of second entries being a particular second entry associated with a particular second offset value, and further comprising:
associating a set of first entries having a set of first offset values with the particular second entry by:
storing a set of first offset values in a subsidiary array at a location associated with a particular subsidiary array offset value, and
storing the particular subsidiary array offset value in the second array at a location designated by the particular second offset value.

7. The method of claim 6, further comprising:

storing, in the second array, a count representing the number of entries of the set of first entries; and wherein the storing the set of first offset values sequentially stores the offset values of the set of first offset values in the subsidiary array.

8. The method of claim 1, wherein the set of entities includes:

a clone entity with a plurality of clone entries, a portion of the plurality of clone entries being a first set of clone entries and having a first set of clone offset values, and a cluster entity with a plurality of cluster entries in a Cluster.Clone attribute array, one of the plurality of cluster entries being a particular cluster entry with an associated particular cluster offset value, and further comprising:
associating the first set of clone entries wit the particular cluster entry by
storing the first set of dine entity offset values in a subsidiary array at a location associated with a particular subsidiary array offset value, and
storing the particular subsidiary array offset value in the Cluster.Clone attribute array at a location designated by the particular cluster offset value for the particular cluster entry.

9. The method of claim 8, wherein the cluster entries include high scoring pairs of associated clone entries having a region of sequence homology such that the region of sequence homology comprises a first predetermined number of matches that exceeds a threshold number of matches, wherein the threshold number of matches was increased when the region of sequence homology was not 100% similar.

10. The method of claim 8, wherein the set of entities further comprises a MapPos entity wherein a portion of the entries of the clone entity and a portion of the entries of the cluster entity are associated with the MapPos entity.

11. The method of claim 1, wherein the set of entities includes:
   a tissueclass entity for establishing a predefined hierarchy of tissue classes; and
   a library entity including a library.tissueclass attribute array for associated an entry of the library entity with at least one entry of the tissueclass entity.

12. The method of claim 11, wherein the tissueclass entity has a TissueClass.Name attribute array and a tissueclass.subclass attribute array; and further comprising:
   storing a particular tissueclass name for a particular entry in the TissueClass.Name attribute array, and
   storing a tissueclass offset value in the tissueclass subclass attribute array for the particular entry such that the tissueclass offset value associates another tissueclass entry having a different tissueclass name with the particular tissueclass entry.

13. The method of claim 12, further comprising:
   populating a portion of the tissueclass entity with tissueclass entries having a predetermined relationships among the tissueclass entries as defined by the TissueClass.Name attribute array, a tissueclass.parent attribute array and the tissueclass.sub-class attribute attribute array.

14. The method of claim 1, wherein the set of entities includes:
   a cluster entity;
   a HitID entity associating entries of the cluster entity with entries of the HitID entity, the entries of the HITID entity being identifiers of known biomolecules; and
   a proteinfunction entity for establishing a predefined hierarchy of biomolecules by protein function, having a proteinclass.hitid attribute array for associating entries of the proteinfunction entity with entries of the HitID entity,
   wherein the proteinclass.hitid attribute array associates a biomolecule entry with at least one identifier of a known biomolecule in the HitID entity, allowing a user to search for biomolecular information by protein function and to identify clusters performing that protein function.

15. The method of claim 14, wherein the proteinfunction entity has a proteinfunction.name attribute array and a proteinfunction.subclass attribute array; further comprising:
   storing a particular biomolecular name for a particular entry in the proteinfunction.name attribute array; and
   storing a proteinfunction offset value in the proteinfunction.subclass attribute array for the particular entry such that the proteinfunction offset value associates another proteinfunction entry having a different biomolecule name with the particular proteinfunction entry for establishing a hierarchy of protein functions.

16. An article of manufacture comprising a machine-readable medium having stored thereon instructions to:
   generate a set of entities, each entity storing attributes for a plurality of entries, at least one attribute being stored in an array wherein data associated with an entry is stored at a location in the array, an entity offset designating the location of the data associated with each entry within the array, wherein the same entity offset is used to access data associated with a particular entry for all attributes within the entity; and
   store the generated set of entities in a memory.

17. The article of manufacture of claim 16, wherein at least one entity is a clone entity having a clone name attribute associated with a clone name, and wherein the machine-readable medium further comprises an instruction to:
   generate the clone name attribute as a function of the entity offset of the clone entity.

18. The article of manufacture of claim 16, wherein at least one entity has a first attribute, and wherein the machine-readable medium further comprises an instruction to:
   generate the first attribute value based on the associated entity offset.

19. The article of manufacture of claim 16, wherein the set of attributes includes a first entity and a second entity, and wherein the machine-readable medium further comprises an instruction to:
   store a particular offset value associated with a particular entry of the second entity in the a first array for an entry of the first entity.

20. The article of manufacture of claim 16, wherein the set of entities includes a clone entity and a library entity, and wherein the machine-readable medium further comprises an instruction to:
   store a particular library offset value associated with a particular library entity entry of the library entity in a clone library array for a clone entry of the clone entity.

21. The article of manufacture of claim 16, wherein the set of entities includes:
   a first entity with a plurality of first entries in a first array, and
   a second entity with a plurality of second entries in a second array, one of the plurality of second entries being a particular second entry associated with a particular second offset value, and
   wherein the machine-readable medium further comprises an instruction to:
      associate a set of first entries having a set of first offset values with the particular second entry by:
         storing a set of first offset values in a subsidiary array at a location associated with a particular subsidiary array offset value, and
         storing the particular subsidiary array offset value in the second array at a location designated by the particular second offset value.

22. The article of manufacture of claim 21, wherein the machine-readable medium further comprises an instruction to:
   store, in the second array, a count representing the number of entries of the set of first entries; and
   wherein the instruction to store the set of first offset values sequentially stores the offset values of the set of first offset values in the subsidiary array.

23. The article of manufacture of claim 16, wherein the set of entities includes:
   a clone entity with a plurality of clone entries, a portion of the plurality of clone entries being a first set of clone entries and having a first set of clone offset values, and
   a cluster entity with a plurality of cluster entries in a Cluster.Clone attribute array, one of the plurality of cluster entries being a particular cluster entry with an associated particular cluster offset value, and wherein the machine-readable medium further comprises an instruction to:

associate the first set of clone entries wit the particular cluster entry by storing the first set of dine entity offset values in a subsidiary array at a location associated with a particular subsidiary array offset value, and storing the particular subsidiary array offset value in the Cluster.Clone attribute array at a location designated by the particular cluster offset value for the particular cluster entry.

24. The article of manufacture of claim 23, wherein the cluster entries include high scoring pairs of associated clone entries having a region of sequence homology such that the region of sequence homology comprises a first predetermined number of matches that exceeds a threshold number of matches, wherein the threshold number of matches was increased when the region of sequence homology was not 100% similar.

25. The article of manufacture of claim 23, wherein the set of entities further comprises a MapPos entity wherein a portion of the entries of the clone entity and a portion of the entries of the cluster entity are associated with the MapPos entity.

26. The article of manufacture of claim 16, wherein the set of entities includes:

a tissueclass entity for establishing a predefined hierarchy of tissue classes; and a library entity including a library.tissueclass attribute array for associated an entry of the library entity with at least one entry of the tissueclass entity.

27. The article of manufacture of claim 26, wherein the tissueclass entity has a TissueClass.Name attribute array and a tissueclass.sub-class attribute array; and and wherein the machine-readable medium further comprises instructions to:

store a particular tissueclass name for a particular entry in the TissueClass.Name attribute array, and store a tissueclass offset value in the tissueclass sub-class attribute array for the particular entry such that the tissueclass offset value associates another tissueclass entry having a different tissueclass name with the particular tissueclass entry.

28. The article of manufacture of claim 27, and wherein the machine-readable medium further comprises an instruction to:

populate a portion of the tissueclass entity with tissueclass entries having a predetermined relationships among the tissueclass entries as defined by the TissueClass.Name attribute array, a tissueclass.parent attribute array and the tissueclass.sub-class attribute attribute array.

29. The article of manufacture of claim 16, wherein the set of entities includes:

a cluster entity;

a HitID entity associating entries of the cluster entity with entries of the HitID entity, the entries of the HITID entity being identifiers of known biomolecules; and a proteinfunction entity for establishing a predefined hierarchy of biomolecules by protein function, having a proteinclass.hitid attribute array for associating entries of the proteinfunction entity with entries of the HitID entity, wherein the proteinclass.hitid attribute array associates a biomolecule entry with at least one identifier of a known biomolecule in the HitID entity, allowing a user to search for biomolecular information by protein function and to identify clusters performing that protein function.

30. The article of manufacture of claim 29, wherein the proteinfunction entity has a proteinfunction.name attribute array and a proteinfunction.subclass attribute array; and wherein the machine-readable medium further comprises instructions to:

store a particular biomolecular name for a particular entry in the proteinfunction.name attribute array; and store a proteinfunction offset value in the proteinfunction.subclass attribute array for the particular entry such that the proteinfunction offset value associates another proteinfunction entry having a different biomolecule name with the particular proteinfunction entry for establishing a hierarchy of protein functions.

31. A computer system for a biomolecular database, comprising:

means for generating a set of entities, each entity storing attributes for a plurality of entries, at least one attribute being stored in an array wherein data associated with an entry is stored at a location in the array, an entity offset designating the location of the data associated with each entry within the array, wherein the same entity offset is used to access data associated with a particular entry for all attributes within the entity; and means for storing the generated set of entities in a memory.

* * * * *

UNITED STATES PATENT AND TRADEMARK OFFICE
CERTIFICATE OF CORRECTION

PATENT NO.    : 6,389,428 B1
DATED         : May 14, 2002
INVENTOR(S)   : Philippe E. Rigault et al.

It is certified that error appears in the above-identified patent and that said Letters Patent is hereby corrected as shown below:

Column 20,
Line 11, change "entry of the second entity in the a first array" to -- entry of the second entity in a first array --.
Line 54, change "associating the first set of clone entries wit the" to -- associating the first set of clone entries with the --.
Line 56, change "storing the first set of dine entity offset values" to -- storing the first set of clone entry offset values --.

Column 21,
Line 13, change "array for associated an entry of the library" to -- array for associating an entry of the library --.

Column 22,
Line 25, change "entry of the second entity in the a first array" to -- entry of the second entity in a first array --.

Column 23,
Line 5, change "associate the first set of clone entries wit the particular" to -- associate the first set of clone entries with the particular --.
Line 7, change "storing the first set of dine entity offset values" to -- storing the first set of clone entry offset values --.
Line 32, change "array for associated an entry of the library" to -- array for associating an entry of the library --.

Signed and Sealed this

Twenty-eighth Day of October, 2003

JAMES E. ROGAN
*Director of the United States Patent and Trademark Office*